(12) United States Patent
Kang et al.

(10) Patent No.: US 9,206,134 B2
(45) Date of Patent: Dec. 8, 2015

(54) POLYMORPHIC FORMS OF COMPOUNDS AS PROLYL HYDROXYLASE INHIBITOR, AND USES THEREOF

(75) Inventors: Xinshan Kang, Fujian (CN); Wei Long, Beijing (CN); Jianxi Zhang, Beijing (CN); Yunyan Hu, Beijing (CN); Yinxiang Wang, Beijing (CN)

(73) Assignee: BEIJING BETTA PHARMACEUTICALS CO. LTD., Beijing (CN)

( * ) Notice: Subject to any disclaimer, the term of this patent is extended or adjusted under 35 U.S.C. 154(b) by 0 days.

(21) Appl. No.: 14/233,902

(22) PCT Filed: Jul. 23, 2012

(86) PCT No.: PCT/CN2012/079058
§ 371 (c)(1),
(2), (4) Date: Sep. 4, 2014

(87) PCT Pub. No.: WO2013/013609
PCT Pub. Date: Jan. 31, 2013

(65) Prior Publication Data
US 2015/0031721 A1    Jan. 29, 2015

(30) Foreign Application Priority Data

Jul. 22, 2011   (CN) .......................... 2011 1 0207175
Jul. 25, 2011   (CN) .......................... 2011 1 0209657
Jul. 26, 2011   (CN) .......................... 2011 1 0211297

(51) Int. Cl.
*C07D 217/26* (2006.01)
*A61K 31/472* (2006.01)

(52) U.S. Cl.
CPC ............ *C07D 217/26* (2013.01); *A61K 31/472* (2013.01); *C07B 2200/13* (2013.01)

(58) Field of Classification Search
None
See application file for complete search history.

(56) References Cited

U.S. PATENT DOCUMENTS

2006/0276477 A1   12/2006   Klaus et al.
2007/0293575 A1   12/2007   Seeley et al.

FOREIGN PATENT DOCUMENTS

| CN | 101394843 | 3/2009 |
| CN | 101500589 | 8/2009 |
| WO | WO 2004/108681 | 12/2004 |
| WO | WO 2007/070359 | 6/2007 |
| WO | WO 2011/006355 | 1/2011 |

OTHER PUBLICATIONS

International Search Report for International Application No. PCT/CN2012/079058, dated Nov. 15, 2012, from the State Intellectual Property Office, the P.R. China (4 pages).

*Primary Examiner* — Zinna Northington Davis
(74) *Attorney, Agent, or Firm* — Finnegan, Henderson, Farabow, Garrett & Dunner, L.L.P.

(57) ABSTRACT

The present invention relates to the polymorphic forms of the compound of Formula (I), preparation thereof including the preparation of intermediates and pharmaceutical compositions, and use of a polymorph above in the treatment of a disease, a disorder or a condition, or in the manufacturing of a medicament for the treatment of a disease, a disorder or a condition.

(I)

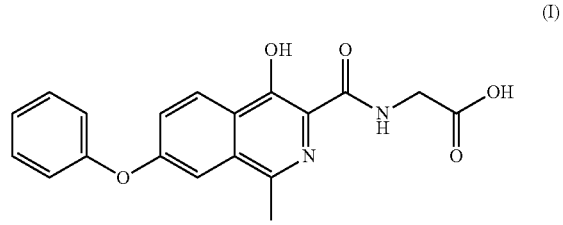

36 Claims, 7 Drawing Sheets

POLYMORPHIC FORMS OF COMPOUNDS AS PROLYL HYDROXYLASE INHIBITOR, AND USES THEREOF

CROSS REFERENCE TO RELATED APPLICATIONS

Figure 1:
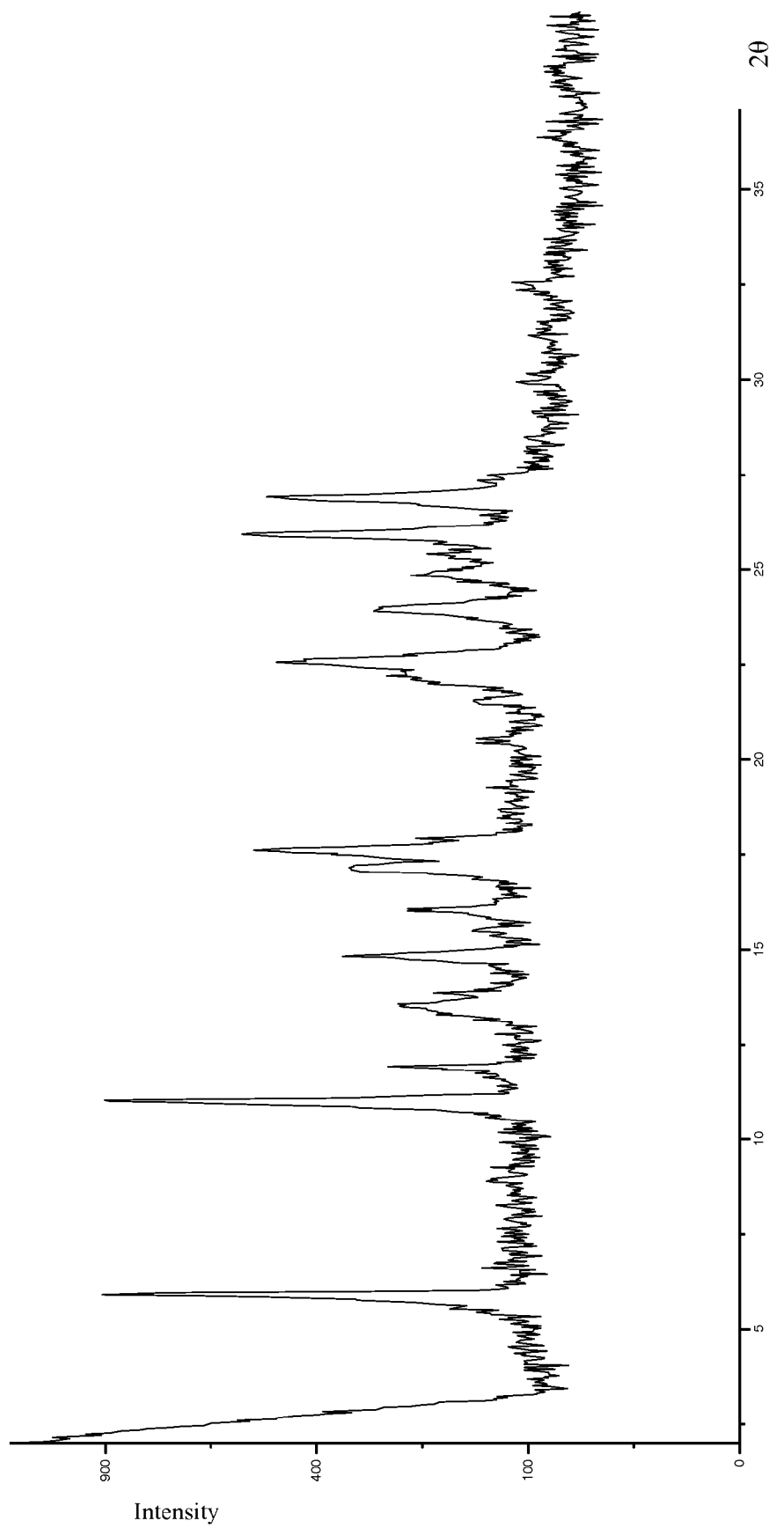

This application is a national phase application based on PCT/CN2012/079058, filed Jul. 23, 2012, which claims the priority of Chinese Patent Application No. 201110207175.6, filed Jul. 22, 2011, Chinese Patent Application No. 201110209657.5, filed Jul. 25, 2011, and Chinese Patent Application No. 201110211297.2, filed Jul. 26, 2011, the contents of all of which are incorporated herein by reference.

FIELD OF THE INVENTION

The present invention relates to the polymorphic forms of a novel compound, and their use in inhibiting prolyl hydroxylase activity. The present invention also relates to a method of using at least one of the polymorphs thereof in modulating HIF level or activity, treating a disease, a disorder or a condition associated with increasing or lowing HIF level or activity, in a subject.

BACKGROUND OF THE INVENTION

The cellular transcription factor HIF (Hypoxia Inducible Factor) occupies a central position in oxygen homeostasis in a wide range of organisms and is a key regulator of responses to hypoxia. The genes regulated by HIF transcriptional activity can play critical roles in angiogenesis, erythropoiesis, hemoglobin F production, energy metabolism, inflammation, vasomotor function, apoptosis and cellular proliferation. HIF can also play a role in cancer, in which it is commonly upregulated, and in the physiological responses to ischemia and hypoxia.

The HIF transcriptional complex comprises an heterodimer (HIFαβ): HIF-β is a constitutive nuclear protein that dimerizes with oxygen-regulated HIF-α subunits. Oxygen regulation occurs through hydroxylation of the HIF-α subunits, which are then rapidly destroyed by the proteasome. In oxygenated cells, the von Hippel-Lindau tumor suppressor protein (pVHL protein) binds to hydroxylated HIF-subunits, thereby promoting their ubiquitin dependent proteolysis. This process is suppressed under hypoxic conditions, stabilizing HIF-α and promoting the transcription and activation of the HIFαβ dimer.

Hydroxylation of HIF-α subunits can occur on proline and asparagine residues and can be catalyzed by a family of 2-oxoglutarate dependent enzymes. This family includes the HIF prolyl hydroxylase isozymes (PHDs), which hydroxylate Pro 402 and Pro 564 of human HIF1α, as well as Factor Inhibiting HIF (FIH), which hydroxylates Asn 803 of human HIF1. Inhibition of FIH or the PHDs leads to HIF stabilization and further transcription and activation.

Inhibition of PHDs also leads to HIF stabilization and promoting transcriptional activation by the HIF complex, which may in turn provide a potential treatment for ischemia or anemia. There have been multiple patents that cover the chemical structure designs of the potential PHDs inhibitors, see, e.g., WO2004108681, WO2007070359 and WO2011006355.

DESCRIPTION OF THE INVENTION

The present invention relates to approximately pure crystalline polymorphs, wherein these polymorphs are the polymorphs of the compound of Formula and/or a hydrate thereof, and/or a solvate thereof.

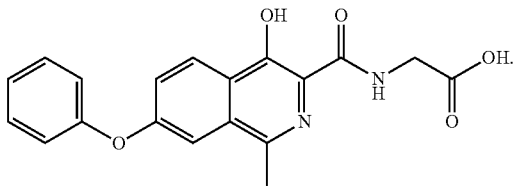

Formula I

The compound of Formula I of the present invention exists in one or more crystal forms. The inventors designated these crystal forms Form I, Form II, Form III, Form IV, Form V, Form VI and Form VII.

The present invention provides a crystalline polymorph of the compound of Formula I that exhibits an X-ray powder diffraction pattern having characteristic peaks at diffraction angles 2θ of approximately 5.9°, 11.0° and 25.9°.

The present invention further provides preferred embodiments of the crystalline polymorph.

Preferably, the X-ray powder diffraction pattern has characteristic peaks, expressed in terms of the interplanar distance, at 14.9 Å, 8.0 Å and 3.4 Å.

Preferably, the X-ray powder diffraction pattern has characteristic peaks at diffraction angles 2θ of approximately 5.9°, 11.0°, 17.6°, 22.6°, 25.9° and 26.9°.

Preferably, the X-ray powder diffraction pattern has characteristic peaks, expressed in terms of the interplanar distance, at 14.9 Å, 8.0 Å, 5.1 Å, 3.9 Å, 3.4 Å and 3.3 Å.

Preferably, the X-ray powder diffraction pattern has characteristic peaks at diffraction angles 2θ of approximately 5.9°, 11.0°, 14.8°, 17.6°, 22.6°, 24.0°, 25.9° and 26.9°.

Preferably, the X-ray powder diffraction pattern has characteristic peaks, expressed in terms of the interplanar distance, at 14.9 Å, 8.0 Å, 6.0 Å, 5.1 Å, 3.9 Å, 3.7 Å, 3.4 Å and 3.3 Å.

Preferably, the X-ray powder diffraction pattern is shown as in FIG. 1.

The X-ray diffraction pattern depicted in FIG. 1 is summarized in Table 1.

TABLE 1

| 2θ (2 theta) ± 0.2 (degrees) | d-spacing [Å] | Intensity |
| --- | --- | --- |
| 5.9 | 14.9 | 664 |
| 11.0 | 8.0 | 781 |
| 14.8 | 6.0 | 213 |
| 17.6 | 5.1 | 404 |
| 22.6 | 3.9 | 362 |
| 24.0 | 3.7 | 137 |
| 25.9 | 3.4 | 398 |
| 26.9 | 3.3 | 365 |

Preferably, the polymorph has a melting point of 174-177° C.

Preferably, the polymorph has a purity of ≥85%.
Preferably, the polymorph has a purity of ≥95%.
Preferably, the polymorph has a purity of ≥99%.

The present also provides a method of preparing the crystalline polymorph, comprising the steps of dissolving the compound of Formula I as prepared in Example 1 in the mixed solvent of methanol/MTBE (methyl tertbutyl ether) at room temperature, followed by a spontaneous precipitation, and recovering the resulted crystalline polymorph.

The present invention also provides a crystalline polymorph of the compound of Formula I that exhibits an X-ray powder diffraction pattern having characteristic peaks at diffraction angles 2θ of approximately 8.2°, 14.5° and 26.6°.

Preferably, the X-ray powder diffraction pattern has characteristic peaks, expressed in terms of the interplanar distance, at 10.8 Å, 6.1 Å and 3.4 Å.

Preferably, the X-ray powder diffraction pattern has characteristic peaks at diffraction angles 2θ of approximately 8.2°, 13.3°, 14.5°, 21.2° and 26.6°.

Preferably, the X-ray powder diffraction pattern has characteristic peaks, expressed in terms of the interplanar distance, at 10.8 Å, 6.7 Å, 6.1 Å, 4.2 Å and 3.4 Å.

Preferably, the X-ray powder diffraction pattern has characteristic peaks at diffraction angles 2θ of approximately 8.2°, 9.6°, 13.3°, 14.5°, 21.2°, 22.8°, 25.4° and 26.6°.

Preferably, the X-ray powder diffraction pattern has characteristic peaks, expressed in terms of the interplanar distance, at 10.8 Å, 9.3 Å, 6.7 Å, 6.1 Å, 4.2 Å, 3.9 Å, 3.5 Å and 3.4 Å.

Figure 2:
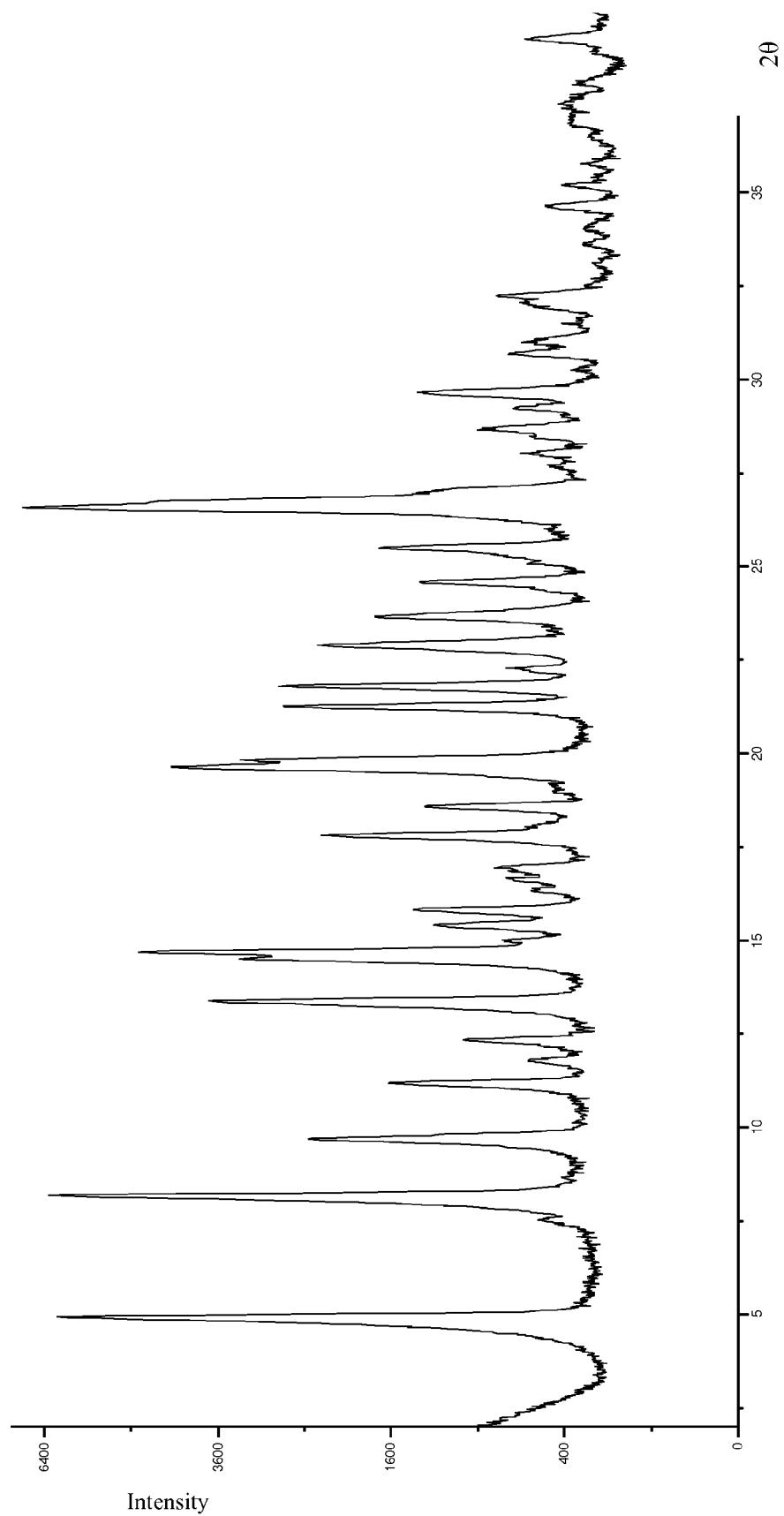

Preferably, the X-ray powder diffraction pattern is shown as in FIG. 2.

The X-ray diffraction pattern depicted in FIG. 2 is summarized in Table 2.

TABLE 2

| 2θ (2 theta) ± 0.2 (degrees) | d-spacing [Å] | Intensity |
|---|---|---|
| 8.2 | 10.8 | 5993 |
| 9.6 | 9.3 | 2100 |
| 13.3 | 6.7 | 3310 |
| 14.5 | 6.1 | 1937 |
| 21.2 | 4.2 | 2409 |
| 22.8 | 3.9 | 1950 |
| 25.4 | 3.5 | 1387 |
| 26.6 | 3.4 | 6403 |

Preferably, the polymorph has a melting point of 209-212° C.

Preferably, the polymorph has a purity of ≥85%.
Preferably, the polymorph has a purity of ≥95%.
Preferably, the polymorph has a purity of ≥99%.

The present invention also provides a method of preparing the crystalline polymorph comprising the steps of slurrying excess amount of the compound of Formula I as prepared in from Example 1 in the mixed solvent of $H_2O$/acetonitrile (3:1), or $H_2O$/ethanol at room temperature or 50° C., or in methanol/$H_2O$ at RT for at least 48 hrs., and recovering the resulted crystalline polymorph.

The present invention further provides a crystalline polymorph of the compound of Formula I that exhibits an X-ray powder diffraction pattern having characteristic peaks at diffraction angles 2θ of approximately 6.2°, 17.8° and 26.2°.

Preferably, the X-ray powder diffraction pattern has characteristic peaks, expressed in terms of the interplanar distance, at 14.3 Å, 5.0 Å and 3.4 Å.

Preferably, the X-ray powder diffraction pattern has characteristic peaks at diffraction angles 2θ of approximately 6.2°, 17.8°, 22.0°, 26.2° and 26.9°.

Preferably, the X-ray powder diffraction pattern having characteristic peaks, expressed in terms of the interplanar distance, at 14.3 Å, 5.0 Å, 4.0 Å, 3.4 Å and 3.3 Å.

Preferably, the X-ray powder diffraction pattern has characteristic peaks at diffraction angles 2θ of approximately 6.2°, 12.1°, 15.6°, 17.8°, 22.0°, 26.2°, 26.9° and 28.9°.

Preferably, the X-ray powder diffraction pattern has characteristic peaks, expressed in terms of the interplanar distance, at 14.3 Å, 7.3 Å, 5.7 Å, 5.0 Å, 4.0 Å, 3.4 Å, 3.3 Å and 3.1 Å.

Preferably, the polymorph has a purity of ≥85%.
Preferably, the polymorph has a purity of ≥95%.
Preferably, the polymorph has a purity of ≥99%.

Figure 3:
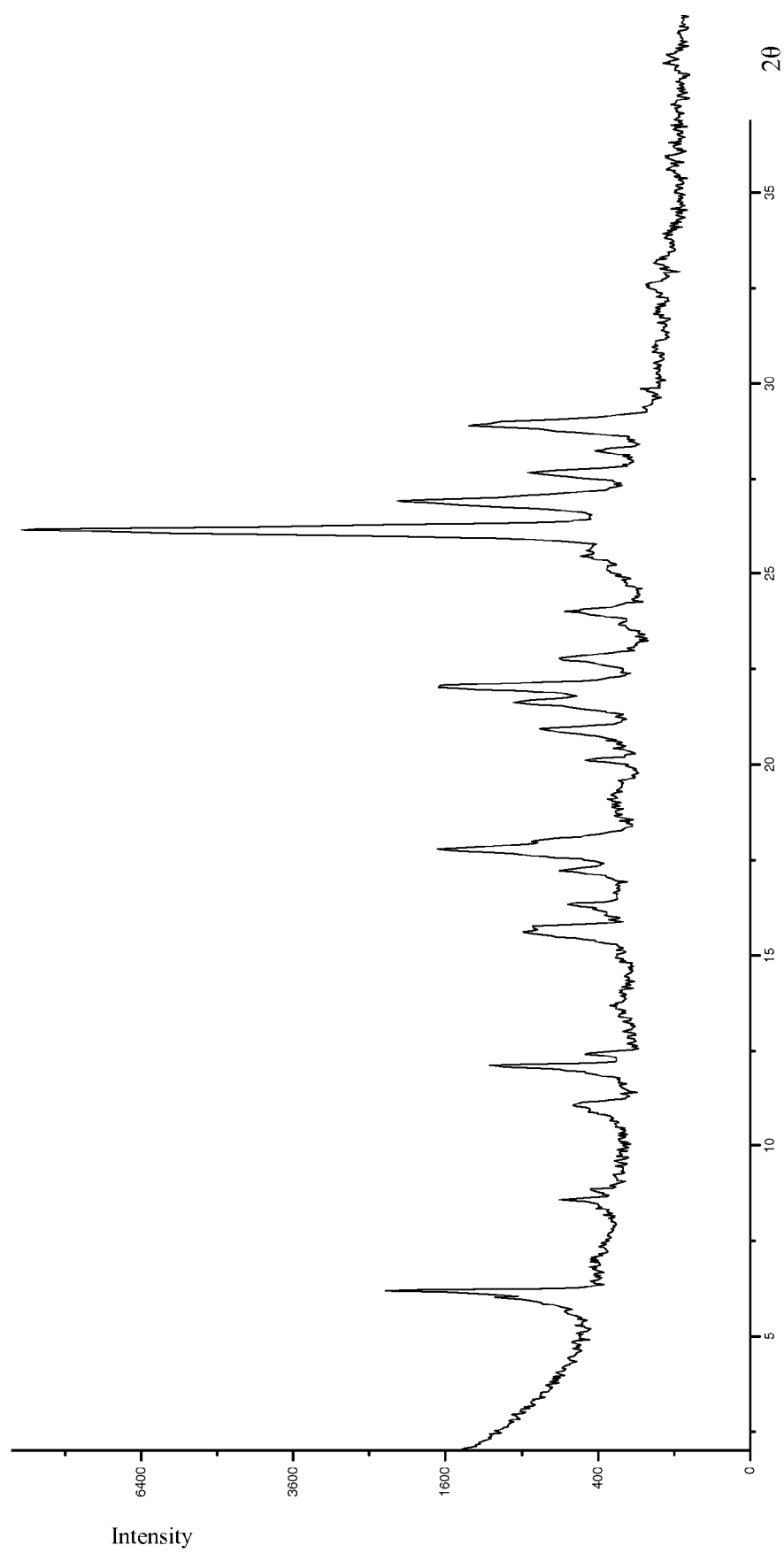

Preferably, the X-ray powder diffraction pattern is shown as in FIG. 3.

The X-ray diffraction pattern depicted in FIG. 3 is summarized in Table 3.

TABLE 3

| 2θ (2 theta) ± 0.2 (degrees) | d-spacing [Å] | Intensity |
|---|---|---|
| 6.2 | 14.3 | 1568 |
| 12.1 | 7.3 | 845 |
| 15.6 | 5.7 | 597 |
| 17.8 | 5.0 | 1391 |
| 22.0 | 4.0 | 1437 |
| 26.2 | 3.4 | 8841 |
| 26.9 | 3.3 | 1933 |
| 28.9 | 3.1 | 1181 |

Preferably, the polymorph has a melting point of 198-200° C.

The present also provides a method of preparing the crystalline polymorph, comprising the steps of: dissolving the compound of Formula I as prepared in Example 1 in the mixed solvent of methanol/acetonitrile at room temperature, followed by a spontaneous precipitation, and recovering the resulted crystalline polymorph; or, comprising the steps of slurrying excess amount of the compound of Formula I as prepared in from Example 1 in $H_2O$, $CH_2Cl_2$, IPAc (Isopropyl Acetate), EtOAc, or IPAc/heptane at 50° C. for at least 48 hrs., and, recovering the resulted crystalline polymorph.

The present invention further provides a crystalline polymorph of the compound of Formula I that exhibits an X-ray powder diffraction pattern having characteristic peaks at diffraction angles 2θ of approximately 12.4°, 20.3° and 26.6°.

Preferably, the X-ray powder diffraction pattern has characteristic peaks, expressed in terms of the interplanar distance, at 7.1 Å, 4.4 Å and 3.4 Å.

Preferably, the X-ray powder diffraction pattern has characteristic peaks at diffraction angles 2θ of approximately 11.3°, 12.4°, 20.3°, 21.4° and 26.6°.

Preferably, the X-ray powder diffraction pattern has characteristic peaks, expressed in terms of the interplanar distance, at 7.9 Å, 7.1 Å, 4.4 Å, 4.1 Å and 3.4 Å.

Preferably, the X-ray powder diffraction pattern has characteristic peaks at diffraction angles 2θ of approximately 11.3°, 12.4°, 15.0°, 17.9°, 20.3°, 21.4°, 24.8° and 26.6°.

Preferably, the X-ray powder diffraction pattern has characteristic peaks, expressed in terms of the interplanar distance, at 7.9 Å, 7.1 Å, 5.9 Å, 5.0 Å, 4.4 Å, 4.1 Å, 3.6 Å and 3.4 Å.

Figure 4:
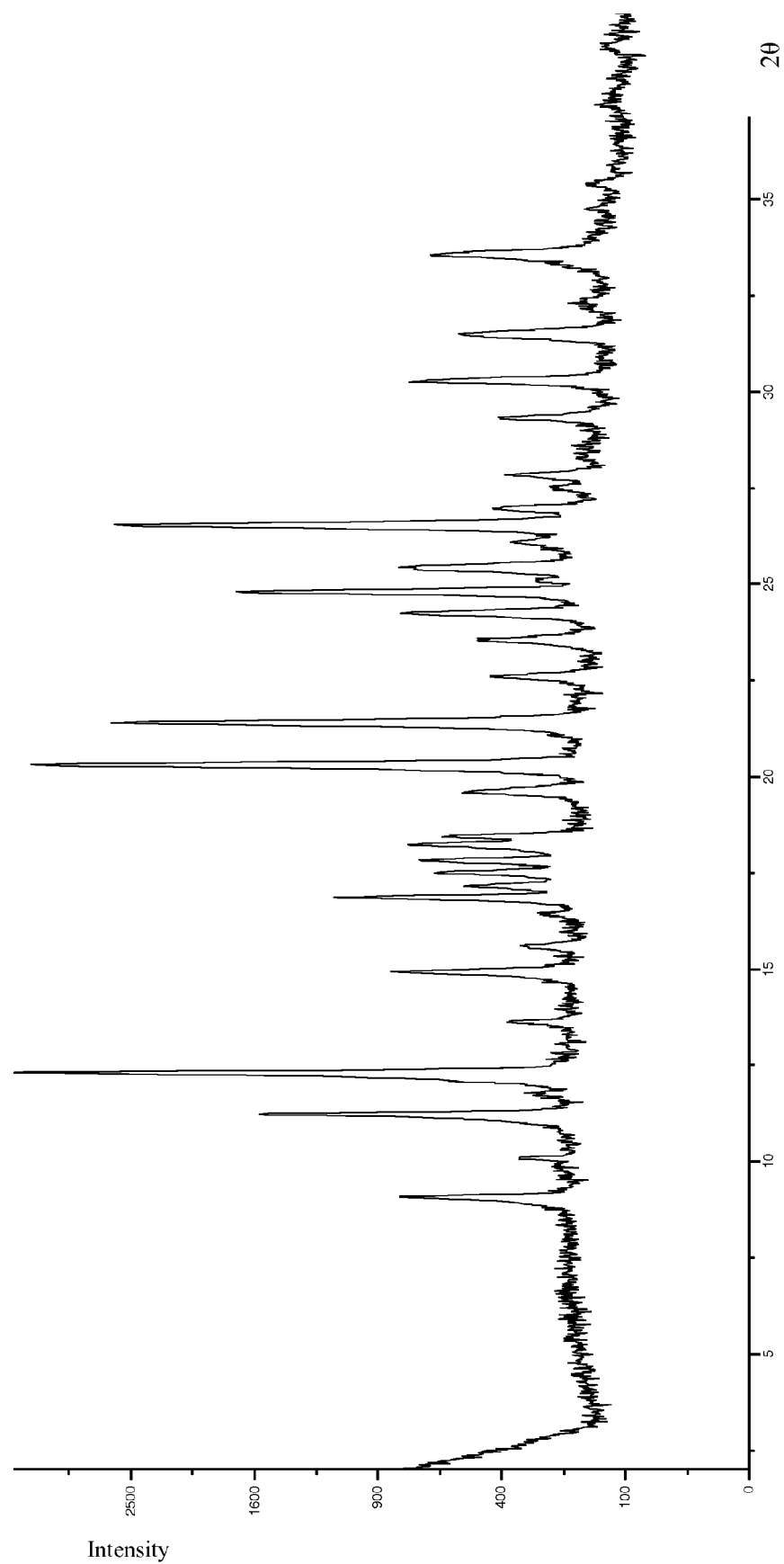

Preferably, the X-ray powder diffraction pattern is shown as in FIG. 4.

The X-ray diffraction pattern depicted in FIG. 4 is summarized in Table 4.

TABLE 4

| 2θ (2 theta) ± 0.2 (degrees) | d-spacing [Å] | Intensity |
|---|---|---|
| 11.3 | 7.9 | 1356 |
| 12.4 | 7.1 | 3288 |
| 15.0 | 5.9 | 448 |
| 17.9 | 5.0 | 3137 |
| 20.3 | 4.4 | 2462 |

TABLE 4-continued

| 2θ (2 theta) ± 0.2 (degrees) | d-spacing [Å] | Intensity |
|---|---|---|
| 21.4 | 4.1 | 1533 |
| 24.8 | 3.6 | 567 |
| 26.6 | 3.4 | 2434 |

Preferably, the polymorph has a melting point of 204-207° C.

Preferably, the polymorph has a purity of ≥85%.
Preferably, the polymorph has a purity of ≥95%.
Preferably, the polymorph has a purity of ≥99%.

The present invention also provides a method of preparing the crystalline polymorph comprising the steps of: slurrying excess amount of the compound of Formula I as prepared in Example 1 in MTBE, the mixed solvent of isopropyl Acetate/heptane or ethyl acetate/heptane at room temperature for at least 48 hrs., and recovering the resulted crystalline polymorph; or, comprising the steps of slurrying excess amount of the compound of Formula I as prepared in Example 1 in the mixed solvent of ethyl acetate/heptane at 50° C. for at least 48 hrs., and recovering the resulted crystalline polymorph; or, comprising the steps of slurrying excess amount of Crystalline Form III of the compound of Formula I as prepared in Example 4 in the mixed solvent of H₂O/acetone at 50° C. for 12-14 days, and recovering the resulted crystalline polymorph.

The present invention further provides a crystalline polymorph of the compound of Formula I that exhibits an X-ray powder diffraction pattern having characteristic peaks at diffraction angles 2θ of approximately 6.0°, 11.1° and 24.1°.

Preferably, the X-ray powder diffraction pattern has characteristic peaks, expressed in terms of the interplanar distance, at 14.8 Å, 8.0 Å and 3.7 Å.

Preferably, the X-ray powder diffraction pattern has characteristic peaks at diffraction angles 2θ of approximately 6.0°, 11.1°, 17.7°, 24.1° and 26.9°.

Preferably, the X-ray powder diffraction pattern has characteristic peaks, expressed in terms of the interplanar distance, at 14.8 Å, 8.0 Å, 5.0 Å, 3.7 Å and 3.3 Å.

Preferably, the X-ray powder diffraction pattern has characteristic peaks at diffraction angles 2θ of approximately 6.0°, 8.8°, 11.1°, 11.9°, 14.9°, 17.7°, 24.1° and 26.9°.

Preferably, the X-ray powder diffraction pattern has characteristic peaks, expressed in terms of the interplanar distance, at 14.8 Å, 10.0 Å, 8.0 Å, 7.4 Å, 6.0 Å, 5.0 Å, 3.7 Å and 3.3 Å.

Figure 5:
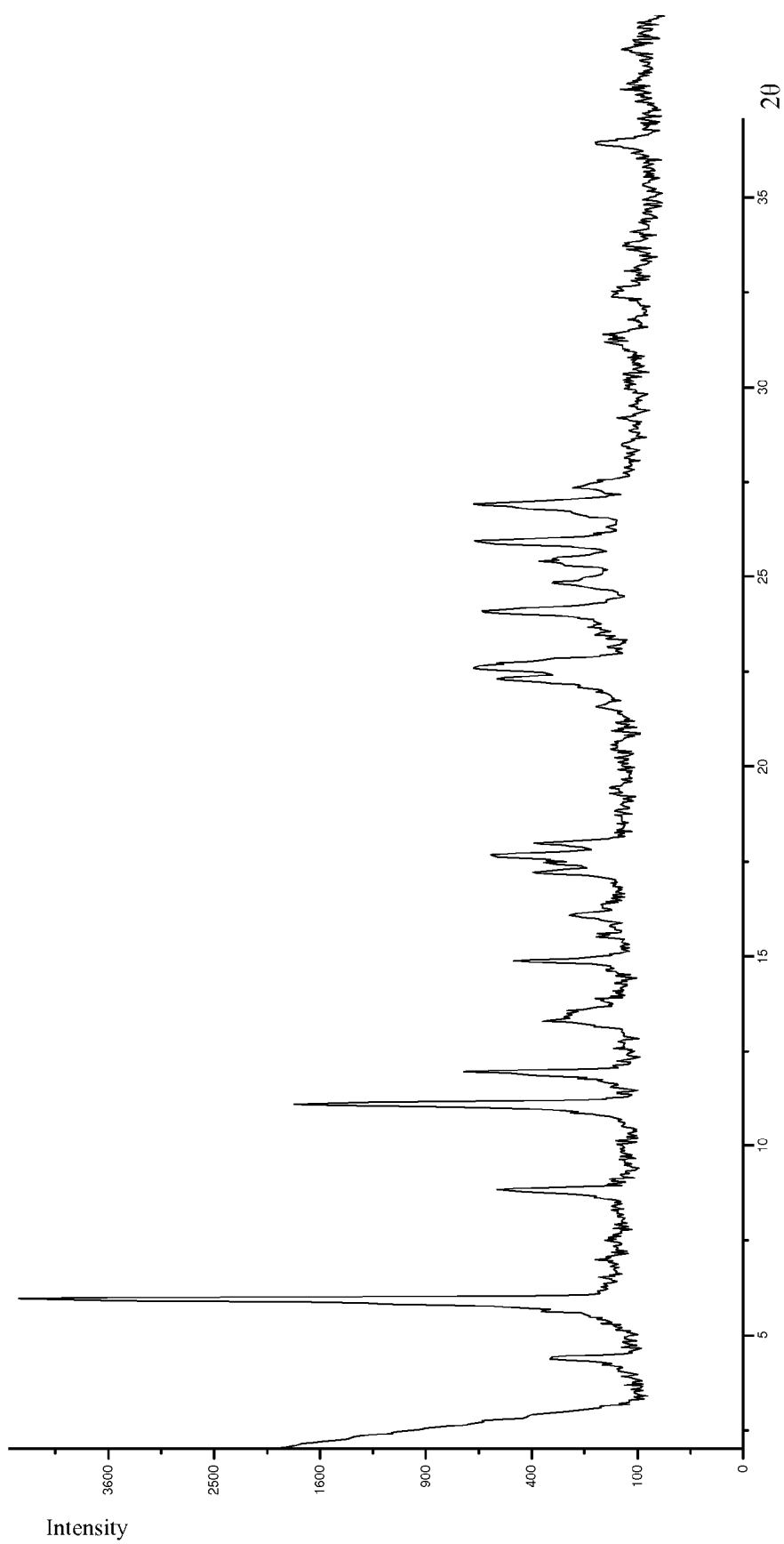

Preferably, the X-ray powder diffraction pattern is shown as in FIG. 5.

The X-ray diffraction pattern depicted in FIG. 5 is summarized in Table 5.

TABLE 5

| 2θ (2 theta) ± 0.2 (degrees) | d-spacing [Å] | Intensity |
|---|---|---|
| 6.0 | 14.8 | 4128 |
| 8.8 | 10.0 | 400 |
| 11.1 | 8.0 | 1526 |
| 11.9 | 7.4 | 565 |
| 14.9 | 6.0 | 342 |
| 17.7 | 5.0 | 441 |
| 24.1 | 3.7 | 480 |
| 26.9 | 3.3 | 512 |

Preferably, the polymorph has a melting point of 190-193° C.

Preferably, the polymorph has a purity of ≥85%.
Preferably, the polymorph has a purity of ≥95%.
Preferably, the polymorph has a purity of ≥99%.

The present invention also provides a method of preparing the crystalline polymorph comprising the steps of slurrying excess amount of the compound of Formula I as prepared in from Example 1 in the mixed solvent of MTBE/heptane at 50° C. for at least 48 hrs., and recovering the resulted crystalline polymorph;

or, adding water as anti-solvent into the methanol solution of the compound of Formula I as prepared in Example 1, and recovering the resulted crystalline polymorph.

The present invention further provides a crystalline polymorph of the compound of Formula I that exhibits an X-ray powder diffraction pattern having characteristic peaks at diffraction angles 2θ of approximately 7.1°, 22.2° and 26.9°.

Preferably, the X-ray powder diffraction pattern has characteristic peaks, expressed in terms of the interplanar distance, at 12.4 Å, 4.0 Å and 3.3 Å.

Preferably, the X-ray powder diffraction pattern has characteristic peaks at diffraction angles 2θ of approximately 7.1°, 10.6°, 18.8°, 22.2° and 26.9°.

Preferably, the X-ray powder diffraction pattern has characteristic peaks, expressed in terms of the interplanar distance, at 12.4 Å, 8.4 Å, 4.7 Å, 4.0 Å and 3.3 Å.

Preferably, the X-ray powder diffraction pattern has characteristic peaks at diffraction angles 2θ of approximately 7.1°, 9.4°, 10.6°, 16.5°, 18.8°, 21.3°, 22.2° and 26.9°.

Preferably, the X-ray powder diffraction pattern has characteristic peaks, expressed in terms of the interplanar distance, at 12.4 Å, 9.4 Å, 8.4 Å, 5.4 Å, 4.7 Å, 4.2 Å, 4.0 Å and 3.3 Å.

Figure 6:
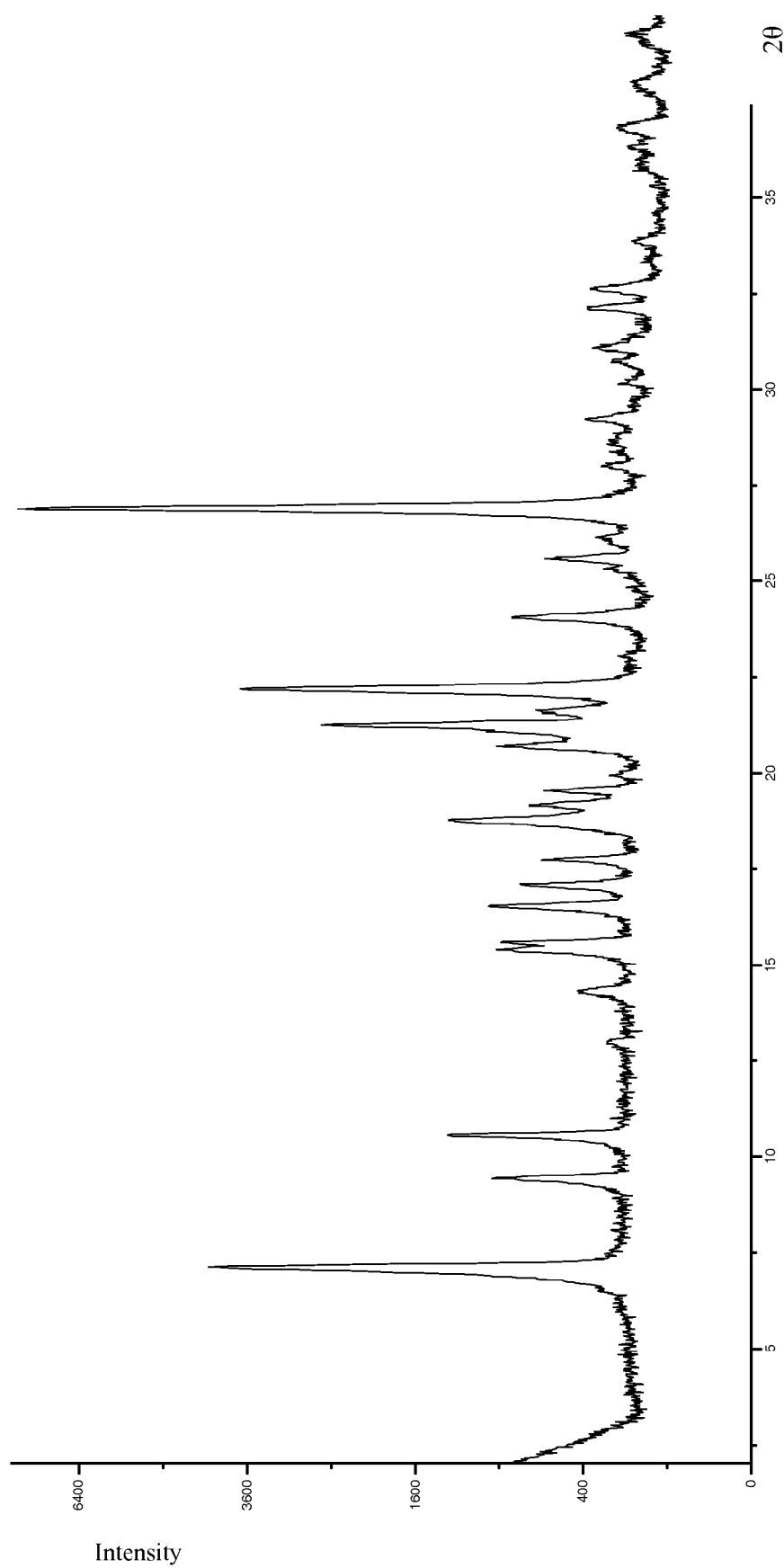

Preferably, the X-ray powder diffraction pattern is shown as in FIG. 6.

The X-ray diffraction pattern depicted in FIG. 6 is summarized in Table 6.

TABLE 6

| 2θ (2 theta) ± 0.2 (degrees) | d-spacing [Å] | Intensity |
|---|---|---|
| 7.1 | 12.4 | 3877 |
| 9.4 | 9.4 | 669 |
| 10.6 | 8.4 | 1077 |
| 16.5 | 5.4 | 732 |
| 18.8 | 4.7 | 1068 |
| 21.3 | 4.2 | 2415 |
| 22.2 | 4.0 | 3446 |
| 26.9 | 3.3 | 7388 |

Preferably, the polymorph has a melting point of 200-203° C.

Preferably, the polymorph has a purity of ≥85%.
Preferably, the polymorph has a purity of ≥95%.
Preferably, the polymorph has a purity of ≥99%.

The present invention also provides a method of preparing the crystalline polymorph comprising the steps of: slurrying excess amount of the compound of Formula I as prepared in the method of Example 1 in the mixed solvent of acetonitrile/H₂O (1:1) or THF/H₂O at room temperature for at least 48 hrs., and recovering the resulted crystalline polymorph;

or, comprising the steps of adding the crystalline polymorph, as prepared in Example 5, as a crystal seed into a solution of the compound of Formula I as prepared in Example 1 in the mixed solvent of methanol/ethyl acetate, followed by a spontaneous precipitation, and recovering the resulted crystalline polymorph.

The present invention further provides a crystalline polymorph of the compound of Formula I that exhibits an X-ray powder diffraction pattern having characteristic peaks at diffraction angles 2θ of approximately 6.9°, 11.7° and 21.1°.

Preferably, the X-ray powder diffraction pattern has characteristic peaks, expressed in terms of the interplanar distance, at 12.8 Å, 7.5 Å and 4.2 Å.

Preferably, the X-ray powder diffraction pattern has characteristic peaks at diffraction angles 2θ of approximately 6.9°, 11.7°, 15.1°, 21.1° and 25.8°.

Preferably, the X-ray powder diffraction pattern has characteristic peaks, expressed in terms of the interplanar distance, at 12.8 Å, 7.5 Å, 5.9 Å, 4.2 Å and 3.5 Å.

Preferably, the X-ray powder diffraction pattern has characteristic peaks at diffraction angles 2θ of approximately 6.9°, 7.5°, 11.7°, 15.1°, 19.3°, 21.1°, 22.6° and 25.8°.

Preferably, the X-ray powder diffraction pattern has characteristic peaks, expressed in terms of the interplanar distance, at 12.8 Å, 11.8 Å, 7.5 Å, 5.9 Å, 4.6 Å, 4.2 Å, 3.9 Å and 3.5 Å.

Figure 7:
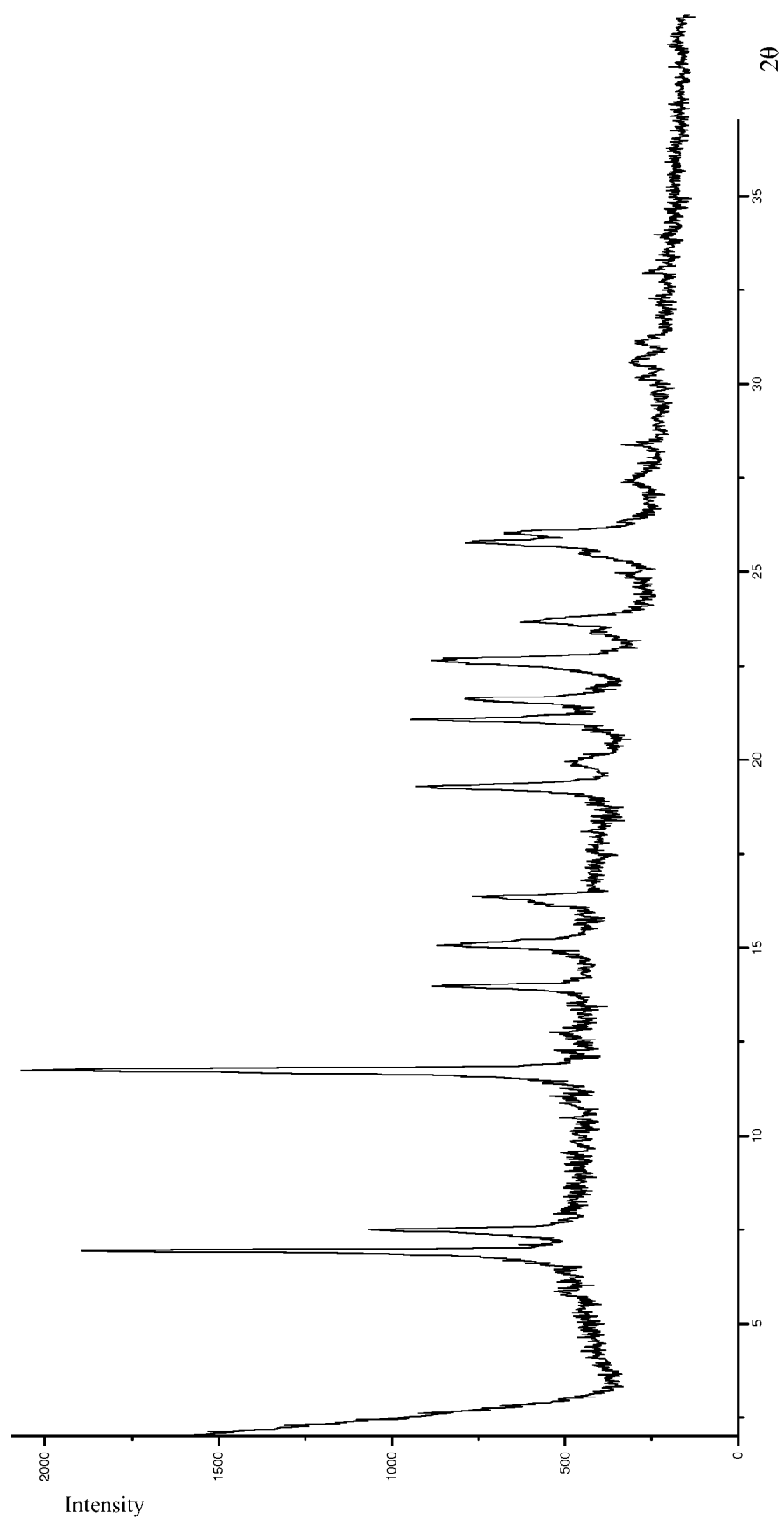

Preferably, the X-ray powder diffraction pattern is shown as in FIG. 7.

The X-ray diffraction pattern depicted in FIG. 7 is summarized in Table 7.

TABLE 7

| 2θ (2 theta) ± 0.2 (degrees) | d-spacing [Å] | Intensity |
|---|---|---|
| 6.9 | 12.8 | 1478 |
| 7.5 | 11.8 | 580 |
| 11.7 | 7.5 | 1604 |
| 15.1 | 5.9 | 289 |
| 19.3 | 4.6 | 469 |
| 21.1 | 4.2 | 375 |
| 22.6 | 3.9 | 486 |
| 25.8 | 3.5 | 471 |

Preferably, the polymorph has a purity of ≥85%.
Preferably, the polymorph has a purity of ≥95%.
Preferably, the polymorph has a purity of ≥99%.

The present invention further provides a method of preparing the crystalline polymorph comprising the steps of heating the Crystalline Form VI as prepared in Example 7 to 180° C., and recovering the resulted crystalline polymorph.

The present invention further provides the use of these crystalline polymorphs.

A pharmaceutical composition comprises a therapeutically effective amount of crystalline polymorphs of the present invention, and a pharmaceutically acceptable excipient, adjuvant or carrier.

The present invention also provides preferable embodiments of the pharmaceutical composition.

Preferably, the pharmaceutical composition comprises a therapeutically effective amount of a crystalline polymorph of the present invention, in combination with at least one of additional active ingredient.

Preferably, the pharmaceutical composition is used in an oral administration.

Preferably, the pharmaceutical composition is used in tablets or capsules.

Preferably, the pharmaceutical composition comprises 1 wt %-99 wt % of the crystalline polymorph of the present invention.

Preferably, the pharmaceutical composition comprises 1 wt %-70 wt % of the crystalline polymorph of the present invention.

Preferably, the pharmaceutical composition comprises 10 wt %-30 wt % of the crystalline polymorph of the present invention.

The crystalline polymorphs of the present invention can be used in manufacturing a medicament for modulating HIF level or HIF activity in a subject.

The present invention also provides preferable embodiments of the uses of the crystalline polymorphs.

Preferably, the crystalline polymorphs of the present invention can be used in manufacturing a medicament for the treatment of a disease, a disorder, or a condition associated with HIF level or HIF activity.

Preferably, the crystalline polymorphs of the present invention can be used in manufacturing a medicament for the treatment of ischemia, anemia, or a disease, disorder, or condition associated with ischemia or anemia.

Preferably, the crystalline polymorphs of the present invention can be used in manufacturing a medicament for the treatment of a disease, a disorder, or a condition selected from ischemia, anemia, wound healing, auto-transplantation, allo-transplantation, xeno-transplantation, systemic high blood pressure, thalassemia, diabetes, cancer or an inflammatory disorder, or a combination of two or more thereof, in a subject.

Also provided is a method of modulating HIF levels or activity in a subject by administering to the subject one crystalline polymorph of the present invention.

Further provided is a method for treating a disease, a disorder, or a condition associated with HIF level or HIF activity in a subject by administering to the subject one crystalline polymorph of the present invention.

Additionally provided is a method for treating ischemia, anemia, or a disease, a disorder or a condition associated with ischemia or anemia in a subject by administering to the subject one crystalline polymorph of the present invention.

Yet additionally provided is a method for treating a disease, a disorder, or a condition selected from ischemia, anemia, wound healing, auto-transplantation, allo-transplantation, xeno-transplantation, systemic high blood pressure, thalassemia, diabetes, cancer or an inflammatory disorder, or a combination of two or more thereof, in a subject by administering to the subject one crystalline polymorph of the present invention.

All the crystalline polymorphs of the present invention are approximately pure.

The term "approximately pure" as herein used refers to at least 85 wt %, preferably at least 95 wt %, more preferably at least 99 wt % of the compound of Formula I exists in a crystal form of the present invention, particularly in the crystal forms of Form I, Form II, Form III, Form IV, Form V, Form VI or Form VII.

The main peaks described in the crystalline polymorphs above are reproducible and are within the error limit (the specified value ±0.2).

In the present invention, "the X-ray powder diffraction pattern shown as in FIG. 1" refers to the X-ray powder diffraction pattern that show major peaks as in FIG. 1, wherein major peaks refer to those with the relative intensity greater than 10%, preferably greater than 30%, relative to the highest peak (with its relative intensity designated to be 100%) in FIG. 1. Likewise, in the present invention, the X-ray powder diffraction pattern shown as in FIG. 2, 3, 4, 5, 6 or 7 refers to the X-ray powder diffraction pattern that show major peaks as in FIG. 2, 3, 4, 5, 6 or 7, wherein major peaks refer to those with the relative intensity greater than 10%, preferably greater than 30%, relative to the highest peak (with its relative intensity designated to be 100%) in FIG. 2, 3, 4, 5, 6 or 7, respectively.

The present invention also provides a method of preparing the compound of Formula I, as follows,

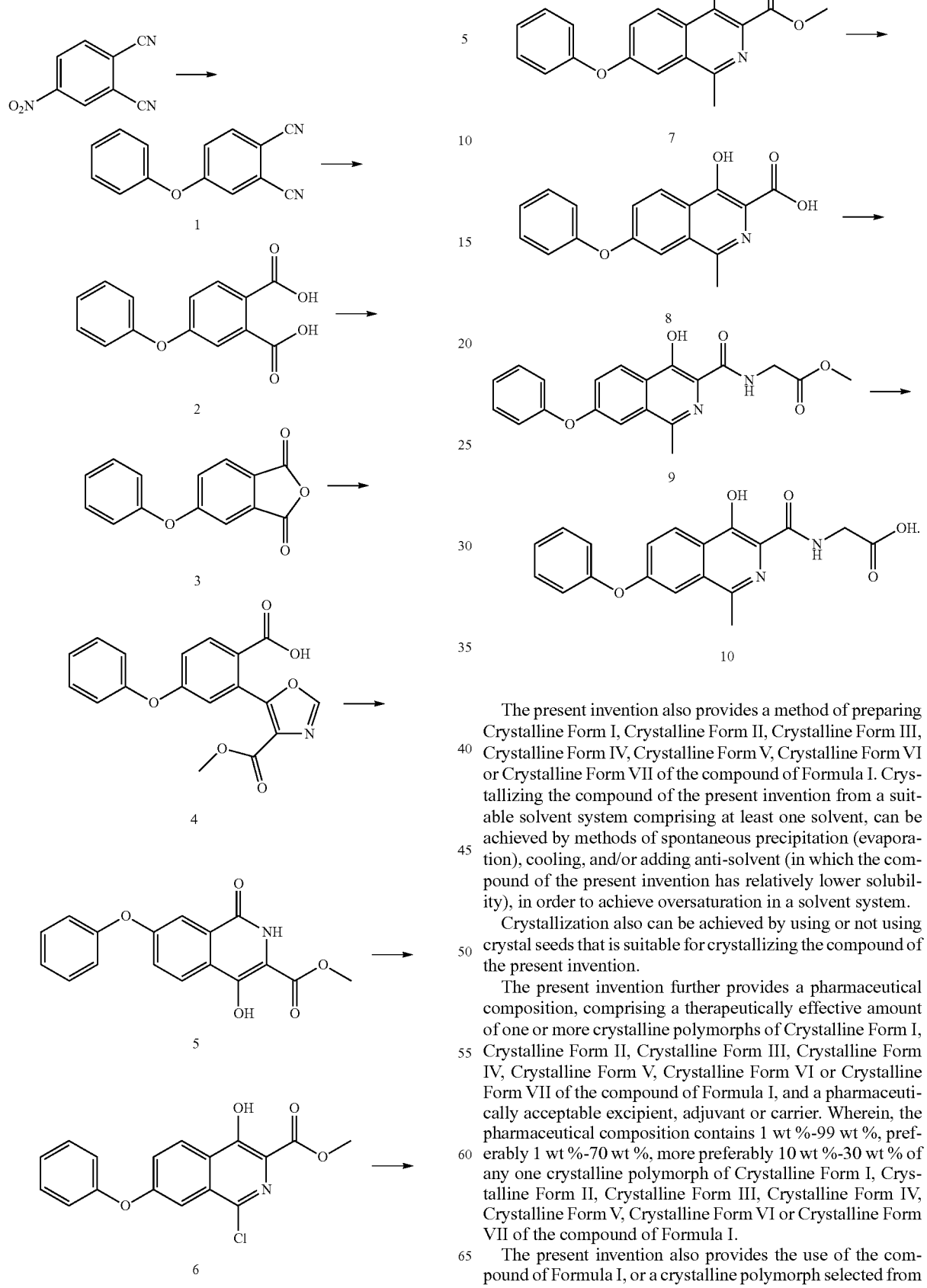

The present invention also provides a method of preparing Crystalline Form I, Crystalline Form II, Crystalline Form III, Crystalline Form IV, Crystalline Form V, Crystalline Form VI or Crystalline Form VII of the compound of Formula I. Crystallizing the compound of the present invention from a suitable solvent system comprising at least one solvent, can be achieved by methods of spontaneous precipitation (evaporation), cooling, and/or adding anti-solvent (in which the compound of the present invention has relatively lower solubility), in order to achieve oversaturation in a solvent system.

Crystallization also can be achieved by using or not using crystal seeds that is suitable for crystallizing the compound of the present invention.

The present invention further provides a pharmaceutical composition, comprising a therapeutically effective amount of one or more crystalline polymorphs of Crystalline Form I, Crystalline Form II, Crystalline Form III, Crystalline Form IV, Crystalline Form V, Crystalline Form VI or Crystalline Form VII of the compound of Formula I, and a pharmaceutically acceptable excipient, adjuvant or carrier. Wherein, the pharmaceutical composition contains 1 wt %-99 wt %, preferably 1 wt %-70 wt %, more preferably 10 wt %-30 wt % of any one crystalline polymorph of Crystalline Form I, Crystalline Form II, Crystalline Form III, Crystalline Form IV, Crystalline Form V, Crystalline Form VI or Crystalline Form VII of the compound of Formula I.

The present invention also provides the use of the compound of Formula I, or a crystalline polymorph selected from Crystalline Form I, Crystalline Form II, Crystalline Form III, Crystalline Form IV, Crystalline Form V, Crystalline Form VI and Crystalline Form VII thereof, in manufacturing a medicament for modulating HIF level or HIF activity.

The present invention also provides a use of the compound of Formula I, or a crystalline polymorph selected from Crystalline Form I, Crystalline Form II, Crystalline Form III, Crystalline Form IV, Crystalline Form V, Crystalline Form VI and Crystalline Form VII thereof, in manufacturing a medicament for the treatment of ischemia, anemia, or a disease, disorder or condition associated with ischemia or anemia.

Further, the present invention also provides a use of the compound of Formula I, or a crystalline polymorph selected from Crystalline Form I, Crystalline Form II, Crystalline Form III, Crystalline Form IV, Crystalline Form V, Crystalline Form VI and Crystalline Form VII thereof, in manufacturing a medicament for the treatment of a disease, disorder, or condition selected from ischemia, anemia, wound healing, auto-transplantation, allo-transplantation, xeno-transplantation, systemic high blood pressure, thalassemia, diabetes, cancer or an inflammatory disorder, or a combination of two or more thereof.

The term "therapeutically effective amount" as herein used, refers to the amount of a compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combination objects for the effective treatment of a disease, a disorder or a condition.

The pharmaceutical composition comprising the compound of the present invention can be administrated via oral, inhalation, rectal, parenteral or topical administration to a subject who needs treatment. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition of the present invention can be produced by the conventional methods in the pharmaceutical field. For example, the active ingredient can be mixed with one or more excipients, then to make the desired formulation. The "pharmaceutically acceptable carrier" refers to conventional pharmaceutical carriers suitable for the desired pharmaceutical formulation, for example: a diluent, a vehicle such as water, various organic solvents, etc, a filler such as starch, sucrose, etc a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye. Preferably, the excipient is suitable for desired formulation and administration type.

The term "disease" or "disorder" or "condition" refers to any disease, discomfort, illness, symptoms or indications.

DESCRIPTIONS OF THE FIGURES

FIG. 1 shows the X-ray powder diffraction pattern of Crystalline Form I of the compound of Formula I FIG. 2 shows the X-ray powder diffraction pattern of Crystalline Form II of the compound of Formula I FIG. 3 shows the X-ray powder diffraction pattern of Crystalline Form III of the compound of Formula I FIG. 4 shows the X-ray powder diffraction pattern of Crystalline Form IV of the compound of Formula I FIG. 5 shows the X-ray powder diffraction pattern of Crystalline Form V of the compound of Formula I FIG. 6 shows the X-ray powder diffraction pattern of Crystalline Form VI of the compound of Formula I FIG. 7 shows the X-ray powder diffraction pattern of Crystalline Form VII of the compound of Formula I The X-ray powder diffraction (XRPD) patterns shown as in FIGS. 1, 2, 3, 4, 5, 6 and 7 were generated on a PANalytical X-ray Diffraction System with Empyrean console. The diffraction peak positions were calibrated by single crystal silicon which has a 2θ value of 28.443 degree. The K-Alpha radiation of an Empyrean Cu LEF X-ray tube was used as the light source of the X-ray.

EXAMPLES

The present invention is further exemplified, but not limited, by the following examples that illustrate the invention. In the examples of the present invention, the techniques or methods, unless expressly stated otherwise, are conventional techniques or methods in the art.

Example 1

Synthesis of the Compound of Formula I

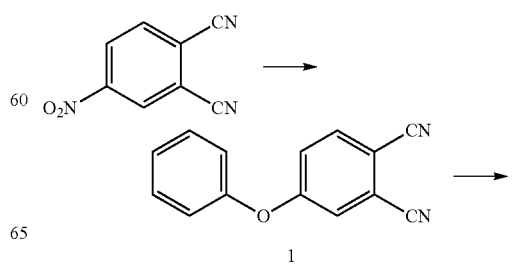

1

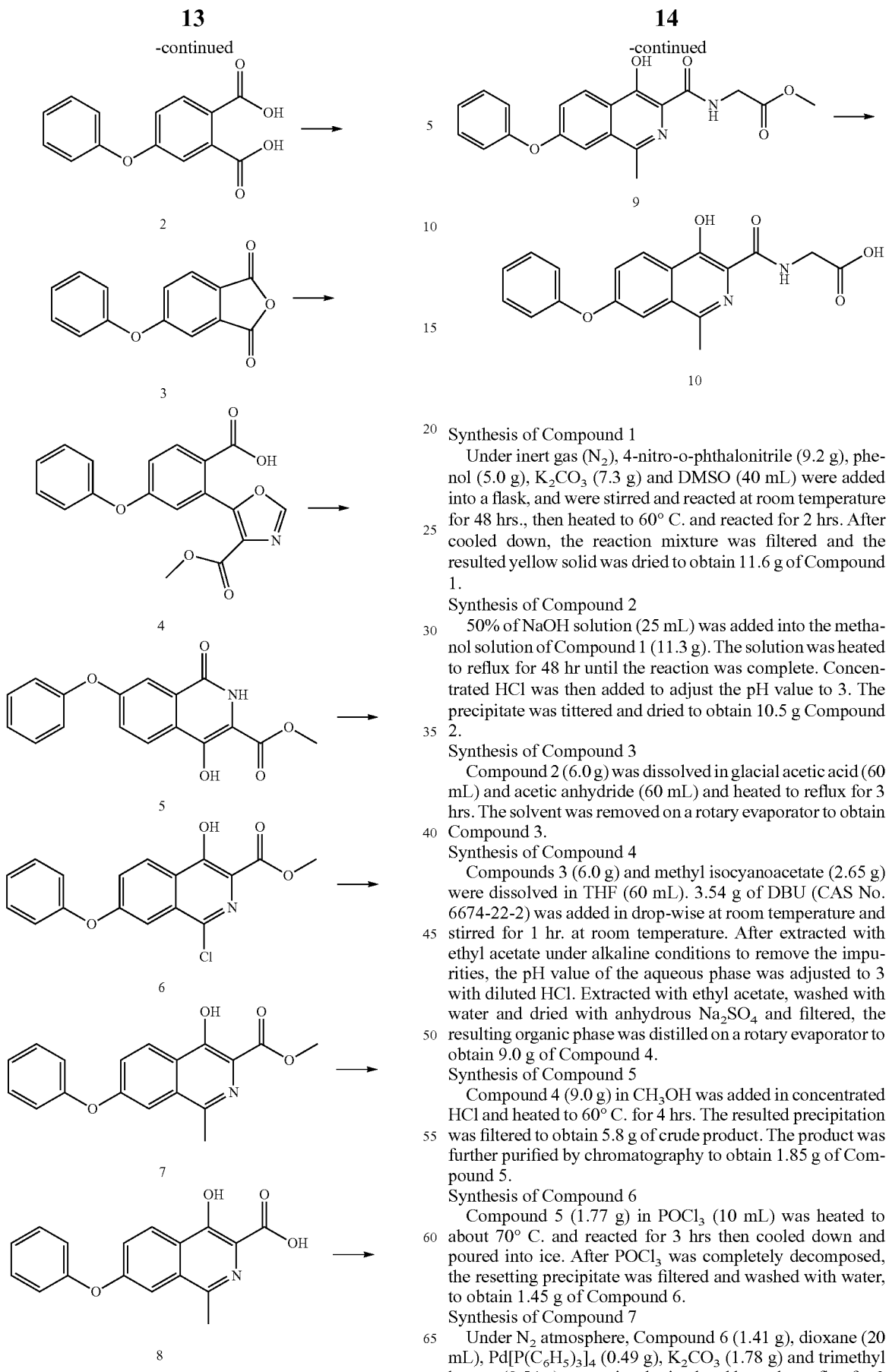

Synthesis of Compound 1

Under inert gas ($N_2$), 4-nitro-o-phthalonitrile (9.2 g), phenol (5.0 g), $K_2CO_3$ (7.3 g) and DMSO (40 mL) were added into a flask, and were stirred and reacted at room temperature for 48 hrs., then heated to 60° C. and reacted for 2 hrs. After cooled down, the reaction mixture was filtered and the resulted yellow solid was dried to obtain 11.6 g of Compound 1.

Synthesis of Compound 2

50% of NaOH solution (25 mL) was added into the methanol solution of Compound 1 (11.3 g). The solution was heated to reflux for 48 hr until the reaction was complete. Concentrated HCl was then added to adjust the pH value to 3. The precipitate was tittered and dried to obtain 10.5 g Compound 2.

Synthesis of Compound 3

Compound 2 (6.0 g) was dissolved in glacial acetic acid (60 mL) and acetic anhydride (60 mL) and heated to reflux for 3 hrs. The solvent was removed on a rotary evaporator to obtain Compound 3.

Synthesis of Compound 4

Compounds 3 (6.0 g) and methyl isocyanoacetate (2.65 g) were dissolved in THF (60 mL). 3.54 g of DBU (CAS No. 6674-22-2) was added in drop-wise at room temperature and stirred for 1 hr. at room temperature. After extracted with ethyl acetate under alkaline conditions to remove the impurities, the pH value of the aqueous phase was adjusted to 3 with diluted HCl. Extracted with ethyl acetate, washed with water and dried with anhydrous $Na_2SO_4$ and filtered, the resulting organic phase was distilled on a rotary evaporator to obtain 9.0 g of Compound 4.

Synthesis of Compound 5

Compound 4 (9.0 g) in $CH_3OH$ was added in concentrated HCl and heated to 60° C. for 4 hrs. The resulted precipitation was filtered to obtain 5.8 g of crude product. The product was further purified by chromatography to obtain 1.85 g of Compound 5.

Synthesis of Compound 6

Compound 5 (1.77 g) in $POCl_3$ (10 mL) was heated to about 70° C. and reacted for 3 hrs then cooled down and poured into ice. After $POCl_3$ was completely decomposed, the resetting precipitate was filtered and washed with water, to obtain 1.45 g of Compound 6.

Synthesis of Compound 7

Under $N_2$ atmosphere, Compound 6 (1.41 g), dioxane (20 mL), $Pd[P(C_6H_5)_3]_4$ (0.49 g), $K_2CO_3$ (1.78 g) and trimethyl borane (0.54 g) were stirred mixed and heated to reflux for 3 hrs., then stirred at room temperature for 48 hrs. After concentration, the resulting mixture was extracted with ethyl acetate, washed with water, dried and filtered, then distilled, on a rotary evaporator, followed by further purification through chromatography, to obtain 0.42 g of Compound 7.

Synthesis of Compound 8

Compound 7 (1.02 g) was added into the mixture of ethanol (10 mL) and 2N of NaOH (10 mL), and refluxed for 1.5 hrs. After removing the impurities by filtration, the resulting mixture was distilled to remove ethanol on a rotary evaporator. The resulting pale yellow precipitate was then filtered, washed with water, and dried to obtain 0.5 of Compound 8.

Synthesis of Compound 9

Compound 8 (0.37 g), glycine methyl ester hydrochloride (0.44 g) and 1.00 g of PyBOP (CAS No. 128625-52-5) were added into dichloromethane (15 mL), and then added triethylamine (0.74 mL) and bis(isopropyl)ethylamine (1.0 mL), stirred and reacted at room temperature for 3 hrs. After filtration, the organic phase was washed with water, dried and filtered, followed by a rotary evaporation, and further purification by a silica gel column, to obtain 0.29 g of Compound 9.

Synthesis of Compound 10, the Compound of Formula I

Compound 9 (0.28 g) in THF was added in 1 N NaOH (5 mL) and stirred and reacted for 1 hr. at mom temperature. After removing THF by a rotary evaporation, the pH value of the residue was adjusted, to about 3 by diluted HCl, washed further by ethyl acetate, filtered, and dried, to obtain 0.21 g of Compound 10, the compound of Formula I.

Example 2

Preparation of Crystalline Form I of the Compound of Formula I

The compound of Formula I prepared from the method disclosed in Example 1 above, was dissolved in the mixed solvent of methanol/MTBE (methyl tertbutyl ether) at room temperature, followed by a spontaneous precipitation to obtain the desired Polymorph Form I, with the melting point of 174-177° C.

Example 3

Preparation of Crystalline Form II of the Compound of Formula I

A slurry suspension of excess amount of the compound of Formula I prepared from the method disclosed in Example 1 above, was stirred in the mixed solvent of $H_2O$/acetonitrile (3:1) or $H_2O$/ethanol at room temperature or 50° C. at least 48 hrs., or in the mixed solvent of methanol/$H_2O$ at room temperature over 48 hr, to obtain the desired Crystalline Form II, with the melting point of 209-212° C.

Example 4

Preparation of Crystalline Form III of the Compound of Formula I

The compound of Formula I prepared from the method disclosed in Example 1 above, was dissolved in the mixed solvent of methanol/acetonitrile at room temperature, followed by a spontaneous precipitation to obtain the desired Crystalline Form III.

Or, a slurry suspension of excess amount of the compound of Formula I prepared from the method disclosed in Example 1 above, was stirred in $H_2O$, $CH_2Cl_2$, isopropyl acetate (IPAc), ethyl acetate (EtOAc), or the mixed solvent of IPAc/heptane or $H_2O$/acetone at 50° C. over 48 hrs., to obtain the desired Crystalline Form III, with the melting point of 198-200° C.

Example 5

Preparation of Crystalline Form IV of the Compound of Formula I

A slurry suspension of excess amount of the compound of Formula I prepared from the method disclosed in Example 1 above, was stirred in MTBE, or the mixed solvent MTBE/heptane, IPAc/heptane, ethyl acetate/heptane or $H_2O$/acetone at room temperature over 48 hrs., to obtain the desired Crystalline Form IV.

Or, a slurry suspension of excess amount of the compound of Formula I prepared from the method disclosed in Example 1 above, was stirred in the mixed solvent of ethyl acetate/heptane at 50° C. over 48 hrs., to obtain the desired Crystalline Form IV.

Or, a slurry suspension of excess amount of the Crystalline Form III as prepared in Example 4 was stirred in the mixed solvent of $H_2O$/acetone at 50° C. for 12-14 days, to obtain the desired Crystalline Form IV, with the melting point of 204-207° C.

Example 6

Preparation of Crystalline Form V of the Compound of Formula I

A slurry suspension of excess amount of the compound of Formula I prepared from the method disclosed in Example 1 above, was stirred in the mixed solvent of MTBE/heptane at 50° C. over 48 hr, to obtain the desired Crystalline Form V; or, water was added as anti-solvent into the methanol solution of the compound of Formula I, to obtain the desired Crystalline Form V, with the melting point of 190-193° C.

Example 7

Preparation of Crystalline Form VI of the Compound of Formula I

A slurry suspension of excess amount of the compound of Formula I prepared from the method disclosed in Example 1 above, was stirred in the mixed solvent of acetonitrile/$H_2O$ (1:1) or THF/$H_2O$ at room temperature over 48 hrs, to obtain the desired Crystalline Form VI.

Or, the compound of Formula I prepared from the method disclosed in Example 1 above, was dissolved in the mixed solvent of methanol/ethyl acetate at room temperature, followed by a spontaneous precipitation using Crystalline Form IV as prepared in Example 5 as crystal seeds to obtain the desired Crystalline Form VI, with the melting point of 200-203° C.

Example 8

Preparation of Crystalline Form VII of the Compound of Formula I

Crystalline Form V prepared from the method of Example 6 was heated to 180° C., to obtain the desired Crystalline Form VII.

Example 9

Assay of HIF-PHD2 Enzyme Activity

HIF-PHD2 activity was measured using homogeneous TR-FRET technology (see also, US2008/004817; Dao J H et al., Anal Biochem. 2009, 384:213-23). To each well of a ½Area 96-well plate was added 2 μL DMSO solution of test compound and 40 μL of assay buffer (50 mM Tris PH7.4/0.01% Tween-20/0.1 mg/ml BSA/1 mM Sodium ascorbate/20 μg/ml Catalase/10 μM FeSO4) containing 600 nM full length PHD2. After a 30 min preincubation at room temperature, the enzymatic reactions were initiated by the addition of 8 μL of substrates (final concentrations of 0.2 μM 2-oxoglutarate and 0.5 μM HIF-1α peptide biotinyl-DLDLEMLAPY-IPMDDDFQL). After 2 hrs. at room temperature, the reactions were terminated and signals were developed by the addition of a 50 μL quench/detection mix to a final concentration of 1 mM ortho-phenanthroline, 0.1 mM EDTA, 0.5 nM anti-$(His)_6$LANCE reagent, 100 nM AF647-labeled Streptavidin, and 30 nM $(His)_6$-VHL-elonginB-elonginC complex. The ratio of time resolved fluorescence signals at 665 and 620 nm was determined, and percent inhibition was calculated relative to an uninhibited control sample run in parallel. For the compound of Formula I prepared from the method disclosed in Example 1 above, the IC50 was determined to be around 2 μM.

Example 10

Determination of Erythropoietin (EPO) Induction in Normal Mice

Eight-week-old male C57BL/6 mice were dosed orally with a suspension of one crystal form of the compound in 0.5% CMC at 20, 60 and 100 mg/kg. Blood samples were obtained from the orbital venous plexus 6 hours after dosing and serum was collected (see also, Robinson A, et al., Gastroenterology. 2008, 134:145-55; Hsieh M M, et al., Blood. 2007, 110:2140-7). Samples were analyzed for EPO by electrochemiluminescence-based immunoassay (MSD) according to manufacturer's instructions. The inducted EPOs when the Crystalline Form VI in this invention was used in suspension were determined to be around 6, 297 and above 300 folds over that of the vehicle group without induction.

Example 11

Stability Determination of Crystal Forms 8.3 mg of the compound of Formula I prepared from the method disclosed in Example 1 above was added into 1 mL of Isopropyl Acetate, stirred and filtered. 9.6 mg of the Crystalline Form IV and 1.97 mg of the Crystalline Form VI disclosed in this invention were then added into the solution and stirred at room temperature for 36 hrs. After centrifugation and drying, the resulted crystal form was determined to be purely the Crystalline Form VI. The Crystalline Form VI was therefore demonstrated to be thermodynamically the most stable crystal form in this study.

What is claimed is:

1. A crystalline form of compound of Formula I,

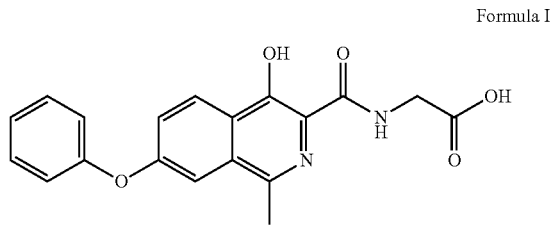 [SMILES: Cc1nc(C(=O)NCC(=O)O)c(O)c2ccc(Oc3ccccc3)cc12]

Formula I characterized by having X-ray powder diffraction pattern with peaks at diffraction angles 2θ of approximately 5.9°, 11.0°, 17.6°, 22.6°, 25.9°, and 26.9°±0.2°.

2. The crystalline form of claim 1, wherein the X-ray powder diffraction pattern further comprises peaks at diffraction angles 2θ of approximately 14.8° and 24.0°±0.2°.

3. The crystalline form of claim 1, wherein the X-ray powder diffraction pattern is substantially in accordance with FIG. 1.

4. The crystalline form of claim 1, characterized by a melting point ranging from about 174° C. to 177° C.

5. A pharmaceutical composition comprising a therapeutically effective amount of at least one compound of Formula I,

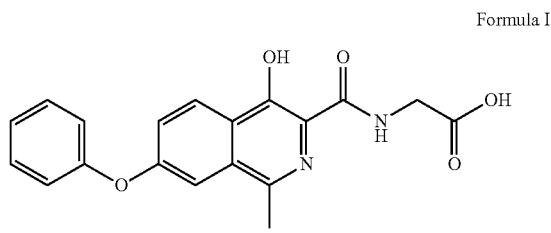 [SMILES: Cc1nc(C(=O)NCC(=O)O)c(O)c2ccc(Oc3ccccc3)cc12]

Formula I and at least one pharmaceutically acceptable carrier, wherein at least 85% of the compound of Formula I is the crystalline form of claim 1.

6. A crystalline form of compound of Formula I,

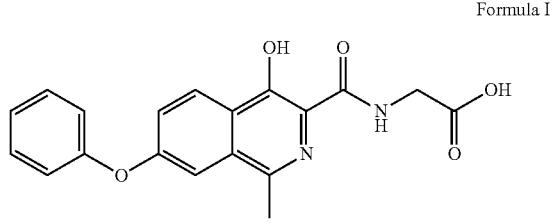 [SMILES: Cc1nc(C(=O)NCC(=O)O)c(O)c2ccc(Oc3ccccc3)cc12]

Formula I characterized by having X-ray powder diffraction pattern with peaks at diffraction angles 2θ of approximately 8.2°, 13.3°, 14.5°, 21.2°, and 26.6°±0.2°.

7. The crystalline form of claim 6, wherein the X-ray powder diffraction pattern further comprises peaks at diffraction angles 2θ of approximately 9.6°, 22.8°, and 25.4°±0.2°.

8. The crystalline form of claim 6, wherein the X-ray powder diffraction pattern is substantially in accordance with FIG. 2.

9. The crystalline form of claim 6, characterized by a melting point ranging from about 209° C. to 212° C.

10. A pharmaceutical composition comprising a therapeutically effective amount of at least one compound of Formula I,

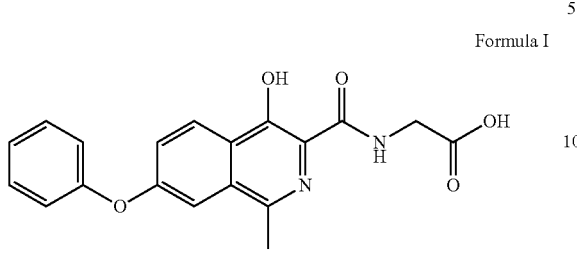

Formula I and at least one pharmaceutically acceptable carrier, wherein at least 85% of the compound of Formula I is the crystalline form of claim 6.

11. A crystalline form of compound of Formula I,

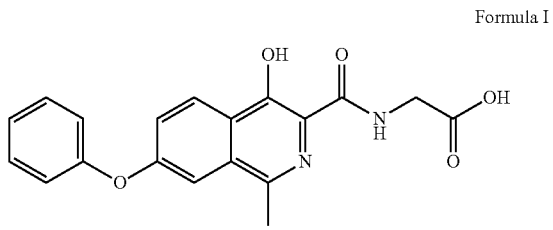 [SMILES: Cc1nc(C(=O)NCC(=O)O)c(O)c2ccc(Oc3ccccc3)cc12]

Formula I characterized by having X-ray powder diffraction pattern with peaks at diffraction angles 2θ of approximately 6.2°, 17.8°, 22.0°, 26.2, and 26.9°±0.2°.

12. The crystalline form of claim 11, wherein the X-ray powder diffraction pattern further comprises peaks at diffraction angles 2θ of approximately 12.1°, 15.6°, and 28.9°±0.2°.

13. The crystalline form of claim 11, wherein the X-ray powder diffraction pattern is substantially in accordance with FIG. 3.

14. The crystalline form of claim 11, characterized by a melting point ranging from about 198° C. to 200° C.

15. A pharmaceutical composition comprising a therapeutically effective amount of at least one compound of Formula I,

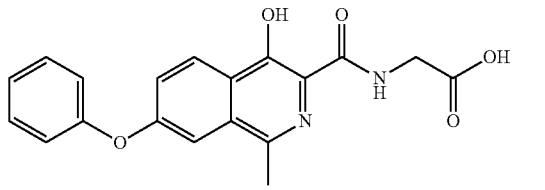

Formula I and at least one pharmaceutically acceptable carrier, wherein at least 85% of the compound of Formula I is the crystalline form of claim 11.

16. A crystalline form of compound of Formula I,

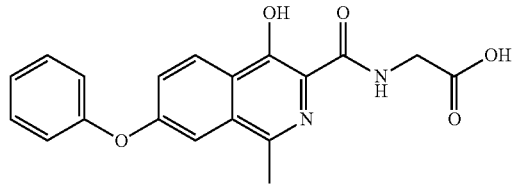

Formula I characterized by having X-ray powder diffraction pattern with peaks at diffraction angles 2θ of approximately 11.3°, 12.4°, 20.3°, 21.4°, and 26.6°±0.2°.

17. The crystalline form of claim 16, wherein the X-ray powder diffraction pattern further comprises peaks at diffraction angles 2θ of approximately 15.0°, 17.9°, and 24.8°±0.2°.

18. The crystalline form of claim 16, wherein the X-ray powder diffraction pattern is substantially in accordance with FIG. 4.

19. The crystalline form of claim 16, characterized by a melting point ranging from about 204° C. to 207° C.

20. A pharmaceutical composition comprising a therapeutically effective amount of at least one compound of Formula I,

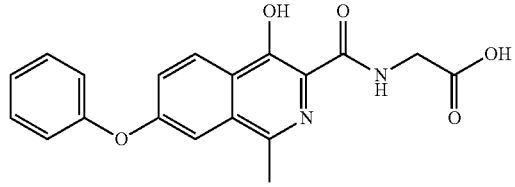

Formula I and at least one pharmaceutically acceptable carrier, wherein at least 85% of the compound of Formula I is the crystalline form of claim 16.

21. A crystalline form of compound of Formula I,

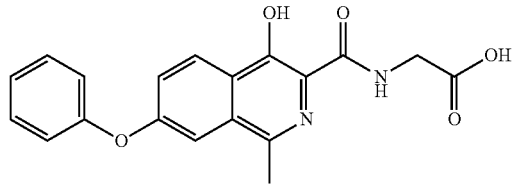

Formula I characterized by having X-ray powder diffraction pattern with peaks at diffraction angles 2θ of approximately 6.0°, 11.1° 17.7°, 24.1°, and 26.9°±0.2°.

22. The crystalline form of claim 21, wherein the X-ray powder diffraction pattern further comprises peaks at diffraction angles 2θ of approximately 8.8°, 11.9°, and 14.9°±0.2°.

23. The crystalline form of claim 21, wherein the X-ray powder diffraction pattern is substantially in accordance with FIG. 5.

24. The crystalline form of claim 21, characterized by a melting point ranging from about 190° C. to 193° C.

25. A pharmaceutical composition comprising a therapeutically effective amount of at least one compound of Formula I,

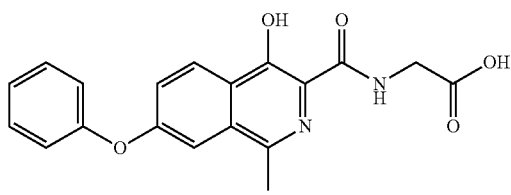

Formula I and at least one pharmaceutically acceptable carrier, wherein at least 85% of the compound of Formula I is the crystalline form of claim 21.

26. A crystalline form of compound of Formula I,

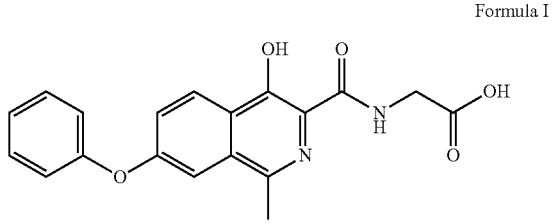 [SMILES: Cc1nc(C(=O)NCC(=O)O)c(O)c2ccc(Oc3ccccc3)cc12]

Formula I characterized by having X-ray powder diffraction pattern with peaks at diffraction angles 2θ of approximately 7.1°, 10.6°, 18.8°, 22.2° and 26.9°±0.2°.

27. The crystalline form of claim 26, wherein the X-ray powder diffraction pattern further comprises peaks at diffraction angles 2θ of approximately 9.4°, 16.5°, and 21.3°±0.2°.

28. The crystalline form of claim 26, wherein the X-ray powder diffraction pattern is substantially in accordance with FIG. 6.

29. The crystalline form of claim 26, characterized by a melting point ranging from about 200° C. to 203° C.

30. A pharmaceutical composition comprising a therapeutically effective amount of at least one compound of Formula I,

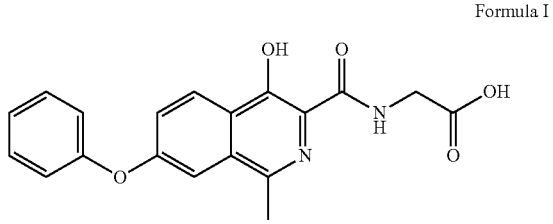 [SMILES: Cc1nc(C(=O)NCC(=O)O)c(O)c2ccc(Oc3ccccc3)cc12]

Formula I and at least one pharmaceutically acceptable carrier, wherein at least 85% of the compound of Formula I is the crystalline form of claim 26.

31. A crystalline form of compound of Formula I,

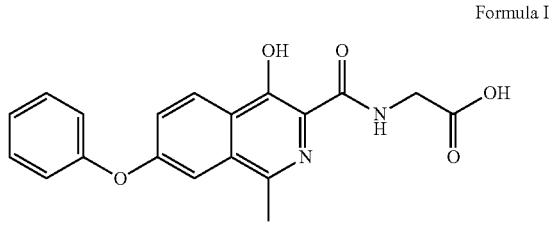 [SMILES: Cc1nc(C(=O)NCC(=O)O)c(O)c2ccc(Oc3ccccc3)cc12]

Formula I characterized by having X-ray powder diffraction pattern with peaks at diffraction angles 2θ of approximately 6.9°, 11.7° 15.1°, 21.1°, and 25.8°±0.2°.

32. The crystalline form of claim 31, wherein the X-ray powder diffraction pattern further comprises peaks at diffraction angles 2θ of approximately 7.5°, 19.3°, and 22.6°±0.2°.

33. The crystalline form of claim 31, wherein the X-ray powder diffraction pattern is substantially in accordance with FIG. 7.

34. A pharmaceutical composition comprising a therapeutically effective amount of at least one compound of Formula I,

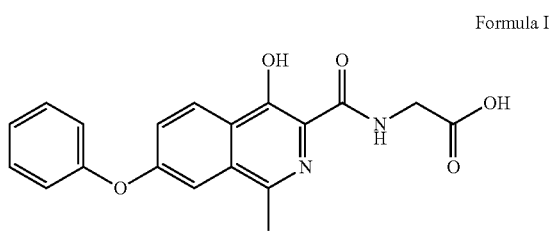 [SMILES: Cc1nc(C(=O)NCC(=O)O)c(O)c2ccc(Oc3ccccc3)cc12]

Formula I and at least one pharmaceutically acceptable carrier, wherein at least 85% of the compound of Formula I is the crystalline form of claim 31.

35. A method for modulating HIF levels or HIF activity in a subject in need thereof comprising administering to the subject a pharmaceutical composition of claim 26.

36. A method of treating a disease, a disorder, or a condition associated with HIF level or HIF activity in a subject in need thereof comprising administering to the subject a pharmaceutical composition of claim 26, wherein the disease, disorder, or condition associated with HIF level or HIF activity is chosen from ischemia, anemia, wound healing, auto-transplantation, allo-transplantation, xeno-transplantation, systemic high blood pressure, thalassemia, diabetes, cancers, and inflammatory disorders.

* * * * *